US006822117B1

(12) United States Patent
Felix et al.

(10) Patent No.: US 6,822,117 B1
(45) Date of Patent: Nov. 23, 2004

(54) METHOD FOR MAKING ADIPIC ACID

(75) Inventors: Albert Felix, Villeurbanne (FR); Yves Roques, Villeurbanne (FR)

(73) Assignee: Rhodia Fiber and Resin Intermediates, Courbevoie (FR)

( * ) Notice: Subject to any disclaimer, the term of this patent is extended or adjusted under 35 U.S.C. 154(b) by 0 days.

(21) Appl. No.: 10/018,814

(22) PCT Filed: Jun. 28, 2000

(86) PCT No.: PCT/FR00/01809

§ 371 (c)(1),
(2), (4) Date: Apr. 22, 2002

(87) PCT Pub. No.: WO01/00557

PCT Pub. Date: Jan. 4, 2001

(30) Foreign Application Priority Data

Jun. 29, 1999 (FR) .............................. 99 08591

(51) Int. Cl.[7] ...................... C07C 51/42; C07C 51/245; C07C 51/27
(52) U.S. Cl. ....................... 562/593; 562/530; 562/513; 562/540
(58) Field of Search ............................... 562/593, 530, 562/513, 540; 560/179

(56) References Cited

U.S. PATENT DOCUMENTS

| 3,123,635 | A | | 3/1964 | Pintauro et al. | |
|---|---|---|---|---|---|
| 4,052,441 | A | * | 10/1977 | Brunner | 560/179 |
| 4,254,283 | A | * | 3/1981 | Mock | 562/530 |
| 4,375,552 | A | * | 3/1983 | Kuceski | 560/204 |
| 5,166,421 | A | * | 11/1992 | Bruner, Jr. | 562/522 |
| 5,471,001 | A | | 11/1995 | Anderson et al. | |
| 5,710,325 | A | * | 1/1998 | Bruner, Jr. et al. | 562/517 |

FOREIGN PATENT DOCUMENTS

| FR | 1 208 145 | 2/1960 |
|---|---|---|
| WO | WO 98/35929 | 8/1998 |

* cited by examiner

*Primary Examiner*—Rita Desai
*Assistant Examiner*—Taylor V. Oh
(74) *Attorney, Agent, or Firm*—Burns, Doane, Swecker & Mathis, L.L.P.

(57) ABSTRACT

The present invention relates to a process for the manufacture of adipic acid, more particularly of adipic acid crystals.

Figure 1:
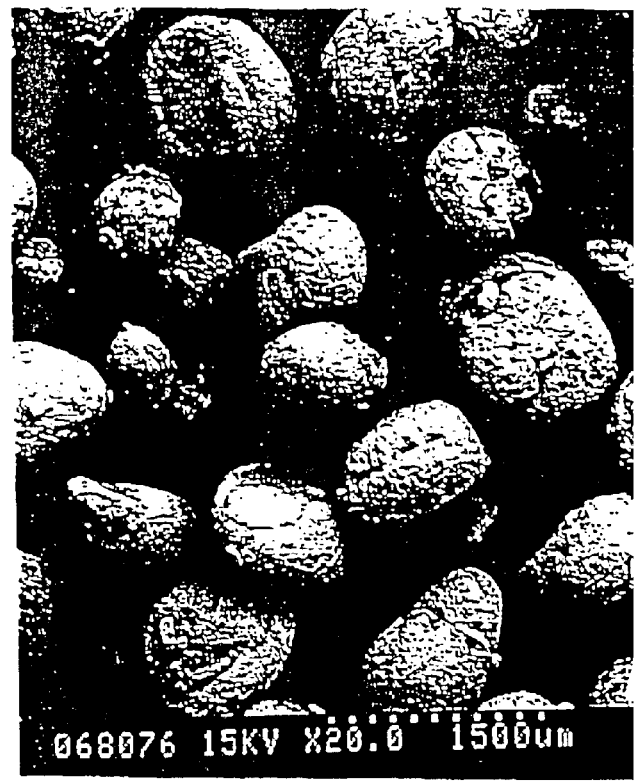

It relates more specifically to a process for the treatment of the adipic acid crystals obtained on conclusion of crystallization, which consists in dispersing the adipic acid crystals collected on conclusion of crystallization in a liquid medium, in stirring the said liquid medium and in then separating the said crystals from the said liquid medium and optionally drying them.

The form of the crystals is modified in order to obtain pebbles with a substantially smooth surface.

7 Claims, 1 Drawing Sheet

METHOD FOR MAKING ADIPIC ACID

The present invention relates to a process for the manufacture of adipic acid, more particularly of adipic acid crystals.

It relates more specifically to a process for the treatment of adipic acid crystals obtained on conclusion of crystallization.

Adipic acid is a major intermediate, in particular in the field of polymers and more particularly of polyamide and in the synthesis of polyurethanes.

Adipic acid is generally synthesized by oxidation of a cyclohexanone/cyclohexanol mixture by nitric acid in the presence of oxidation catalysts, such as vanadium and copper.

The adipic acid is recovered and purified by successive crystallization operations.

During these operations, the adipic acid is separated in particular from the other dicarboxylic acids formed, such as glutaric acid or succinic acid.

The adipic acid crystals produced on conclusion of crystallization are generally oblong in shape and have a very uneven surface.

Adipic acid is generally stored in large tanks or containers and optionally transported to the site of its use, for example plants for the manufacture of polyamide or of hexamethylenediamine adipate salt.

During this storage and optionally transportation, caking often takes place, that is to say a sticking together of several crystals. This phenomenon is highly damaging as it greatly reduces the flowability of adipic acid during the feeding of the crystals in the plants, for example polymerization plants.

Patent U.S. Pat. No. 5,471,001 provides a specific process for the crystallization of adipic acid with the use of ultrasound. The crystals obtained exhibit better flowability and a weaker property of "caking" during storage and transportation.

One of the aims of the present invention is to provide a process which makes possible the manufacture of adipic acid crystals exhibiting a specific shape and a specific surface condition, in order to obtain good flowability during the charging or discharging or more generally the transportation of these crystals and a decreased property of "caking".

To this end, the invention provides a process for the manufacture of adipic acid crystals which consists in treating the crystals obtained after crystallization according to a process comprising the stages of dispersing the said crystals in a liquid medium, of stirring the said liquid medium for a predetermined period of time, in order to obtain the desired shape and the desired surface condition of the crystals, and of then separating the said treated crystals from the said liquid medium.

According to another characteristic of the invention, the liquid medium is preferably water or a water/acetic acid mixture in all proportions.

The temperature conditions for carrying out this treatment, in particular during the stage of stirring the liquid medium, are not critical.

However, it is preferable for the solubility of adipic acid in the liquid medium to remain low in the temperature range chosen, for example at a value of less than approximately 2 g/l at 20° C. The preferred temperature range of the invention is between 20° C. and 70° C., advantageously between 20° C. and 60° C.

In some-cases, it may be advantageous to cool the liquid medium to a temperature of less than 20° C., before separating the crystals from the said liquid medium.

Likewise, the power of the stirring should be sufficient to prevent excessively large concentration gradients for adipic acid or other compounds present in the medium. However, this power should not be too high, in order to avoid breaking up the crystals.

According to a novel characteristic of the invention, the concentration by weight of adipic acid crystals in the liquid medium is greater than 5% (solid mass/solid mass+liquid mass ratio) and advantageously between 5% and 60% by weight.

The concentration of crystals can have an effect on the result of the treatment. This is because the greater the number of crystals, the greater the effect of smoothing the surface of the latter. However, an excessively high concentration can be harmful to the process as it will not make it possible to obtain a correct smoothing effect and can result in an agglomeration of crystals to one another.

According to the invention, it is preferable for the adipic acid crystals intended to be dispersed to exhibit a mean size of between 100 $\mu$m and 1000 $\mu$m, advantageously between 200 and 700 $\mu$m.

These crystals can be subjected to a preliminary milling, if their mean size after crystallization is too high.

After treatment according to the process, the crystals have a mean size of between 50 $\mu$m and 1000 $\mu$m approximately.

However, the mean sizes specified hereinabove are only indicated by way of illustration and correspond to the preferred ranges. The process of the invention can also be applied to crystals with a lower or greater mean size.

According to a preferred embodiment of the invention, the treatment of the crystals is obtained by setting the liquid medium in motion. This setting of the liquid medium in motion can be a stirring of the latter carried out with one or more stirrers exhibiting varied moving forms conventionally used in the field of the stirring of suspensions.

To improve the effect of the treatment, baffles can be positioned in the reactor comprising the liquid medium.

This setting of the liquid medium in motion can also be obtained by rotating the liquid medium in a device of the centrifuge type.

Finally, the invention generally comprises any means and device capable of setting a liquid in motion in a reactor or a vessel. This is because other plants or devices than those described hereinabove might be used without departing, on that account, from the scope of the invention.

Furthermore, the process of the invention makes it possible, if necessary, to wash the adipic acid crystals. Thus, the content of nitric acid is greatly reduced.

The adipic acid crystals treated according to the process of the invention have the form of a pebble with a smooth surface. The pebbles have varied shapes, in particular oblong shapes, exhibiting no sharp ridges.

The crystals thus treated exhibit a low tendency to cake. In addition, their shape, without sharp ridges, and their smooth surface make it possible to obtain ready movement of one agglomerate with respect to another when they are isolated from the liquid medium and dried.

For this reason, the adipic acid crystals obtained by the process of the invention exhibit excellent flowability and a very weak property of caking.

It is therefore possible to store and transport these products for lengthy periods of time and under uncontrolled atmospheric conditions.

It is easy to fill the storage and transportation containers, as well as to remove from stock or to feed to reactors.

Figure 2:
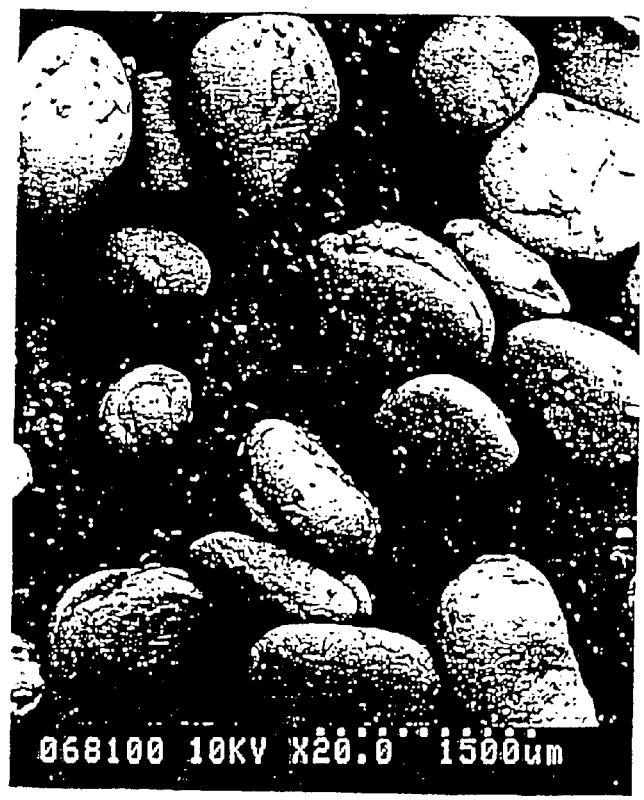

The invention will be better illustrated in the light of the examples hereinbelow, given solely by way of indication, and with reference to the appended figures, in which:

FIG. 1 represents a view taken with a scanning electron microscope with a magnification of 20 of a sample of crystals of adipic acid untreated by the process of the invention, and FIG. 2 represents a view taken with a scanning electron microscope with a magnification of 20 of a sample of the crystals represented in FIG. 1 after treatment by the process of the invention.

Adipic acid crystals obtained by crystallization from an aqueous adipic acid solution have a mean size of 600 µm. The form of these crystals is illustrated in FIG. 1. These crystals form lumps with an oblong shape exhibiting a very uneven surface, comprising small grains stuck to or agglomerated at the surface and numerous cracks or cavities. 200 g of crystals are dispersed in 330 g of water present in a vessel equipped with a stirrer. The concentration of the crystals in the liquid medium is 40% by weight.

The mixture is kept stirred for one hour at a temperature of 25° C.

After filtering and drying in a fluidized bed at 100° C. for one hour, the adipic acid crystals obtained exhibit a mean size of 600 µm.

The appearance of these crystals, illustrated by FIG. 2, clearly shows the effect of the process of the invention. This is because the crystals still have the form of an oblong pebble but their surface is smooth with few adherent particles.

After storing the crystals in a conventional container for several days in a normal atmosphere, feeding them to a reactor did not present any problems. No agglomeration or caking was observed.

What is claimed is:

1. Process for the manufacture of adipic acid crystals from adipic acid obtained by crystallization, comprising dispersing the adipic acid crystals collected on conclusion of crystallization in a liquid medium of water or a water/acetic acid mixture, stirring said liquid medium to smooth the surface of said crystals, and separating said crystals from said liquid medium, wherein the temperature of the liquid medium is between 20° C. and 70° C.

2. Process according to claim 1, wherein the concentration by weight of adipic acid in the liquid medium is greater than or equal to 5%.

3. Process according to claim 2, wherein the concentration by weight of adipic acid in the liquid medium is between 5% and 60%.

4. Process according to claim 1, wherein the adipic acid crystals before dispersion have a mean size of between 100 µm and 1000 µm.

5. Process according to claim 1, wherein the crystals separated from the dispersion have a mean size of between 50 µm and 1000 µm.

6. Process according to claim 1, wherein the liquid medium is cooled before the separation of the treated crystals.

7. A process for treating adipic acid crystals, which comprises:

dispersing said crystals in a liquid medium of water or a water/acetic acid mixture at a temperature between 20° C. and 70° C. to form a mixture of solid and liquid;

setting said mixture in motion to smooth the surface of said crystals; and separating the treated crystals from the liquid medium.

* * * * *